US00PP19849P3

(12) United States Plant Patent
Todd

(10) Patent No.: US PP19,849 P3
(45) Date of Patent: Mar. 24, 2009

(54) PEAR TREE NAMED 'TODD'

(50) Latin Name: *Pyrus communis*
Varietal Denomination: Todd

(76) Inventor: Gary Todd, P.O. Box 216, Entiat, WA (US) 98822-0216

( * ) Notice: Subject to any disclaimer, the term of this patent is extended or adjusted under 35 U.S.C. 154(b) by 0 days.

(21) Appl. No.: 11/895,292

(22) Filed: Aug. 22, 2007

(65) Prior Publication Data

US 2008/0184431 P1 Jul. 31, 2008

Related U.S. Application Data

(60) Provisional application No. 60/839,923, filed on Aug. 23, 2006.

(51) Int. Cl.
*A01H 5/00* (2006.01)

(52) U.S. Cl. ..... Plt./176

(58) Field of Classification Search ..... Plt./176
See application file for complete search history.

*Primary Examiner*—Annette H Para
(74) *Attorney, Agent, or Firm*—Stratton Ballew PLLC

(57) ABSTRACT

A new and distinct pear tree named 'Todd' is disclosed. The new pear is a limb sport of 'Bosc' and is notable for its large, russeted fruit.

4 Drawing Sheets

Latin name of the genus and species of the plant claimed: *Pyrus communis.*
Variety denomination: 'Todd'.

BRIEF DESCRIPTION OF THE PHOTOGRAPHS

BRIEF DESCRIPTION OF THE VARIETY

Figure 1:
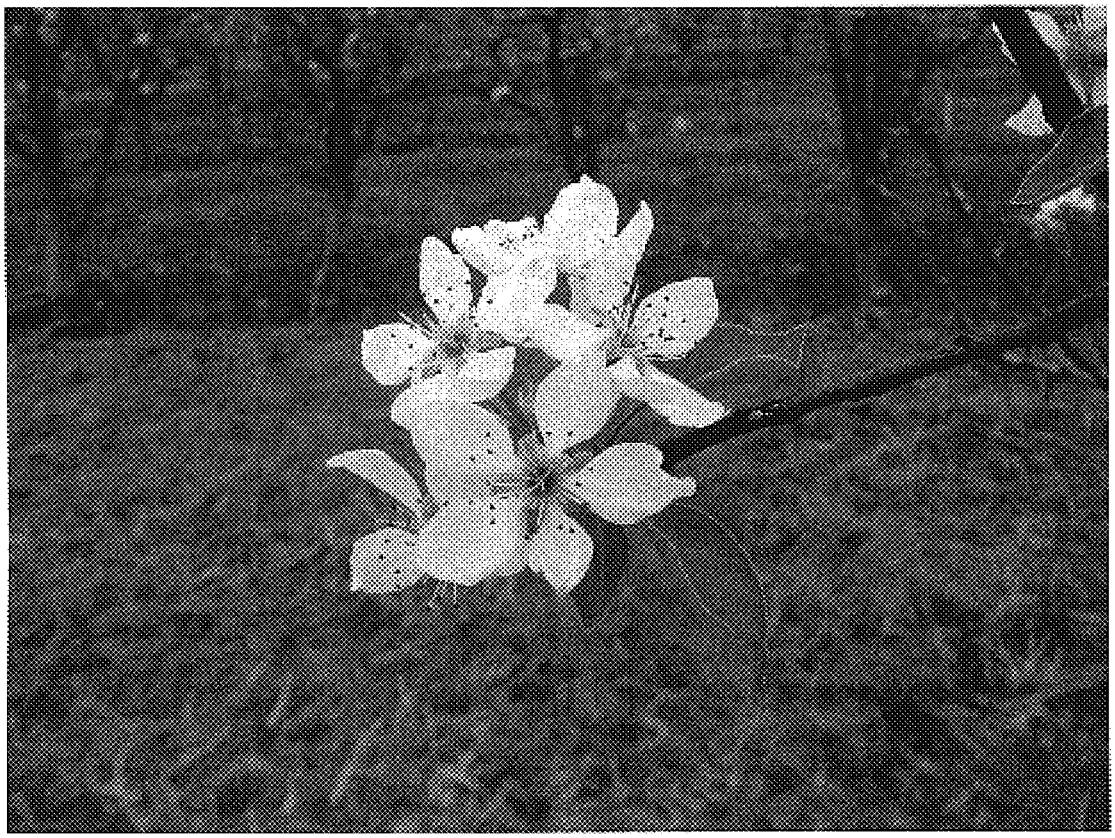
FIG. 1 shows blossoms of the 'Todd' pear tree.
Figure 2:
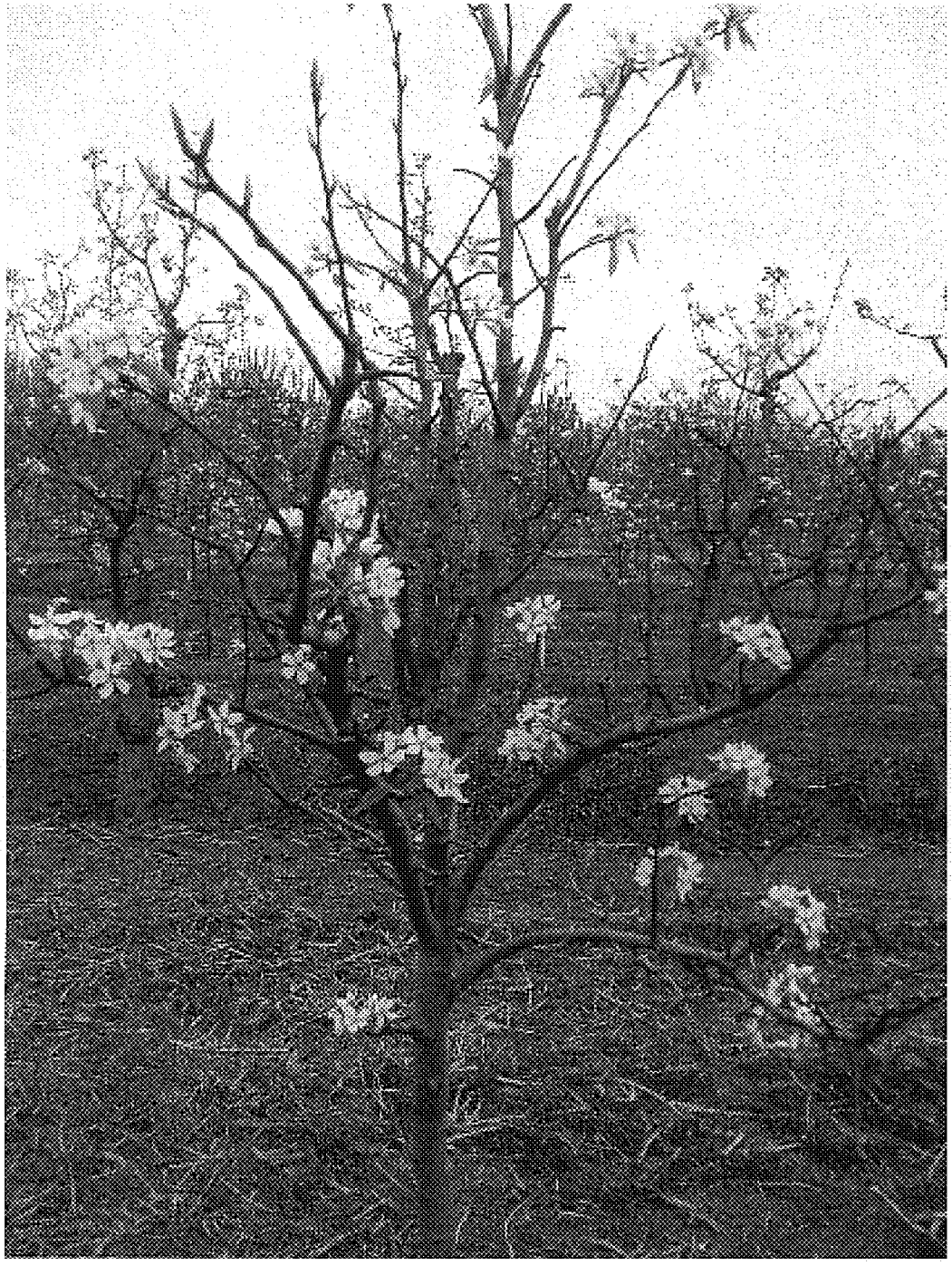
FIG. 2 shows the 'Todd' pear tree in bloom.
Figure 3:
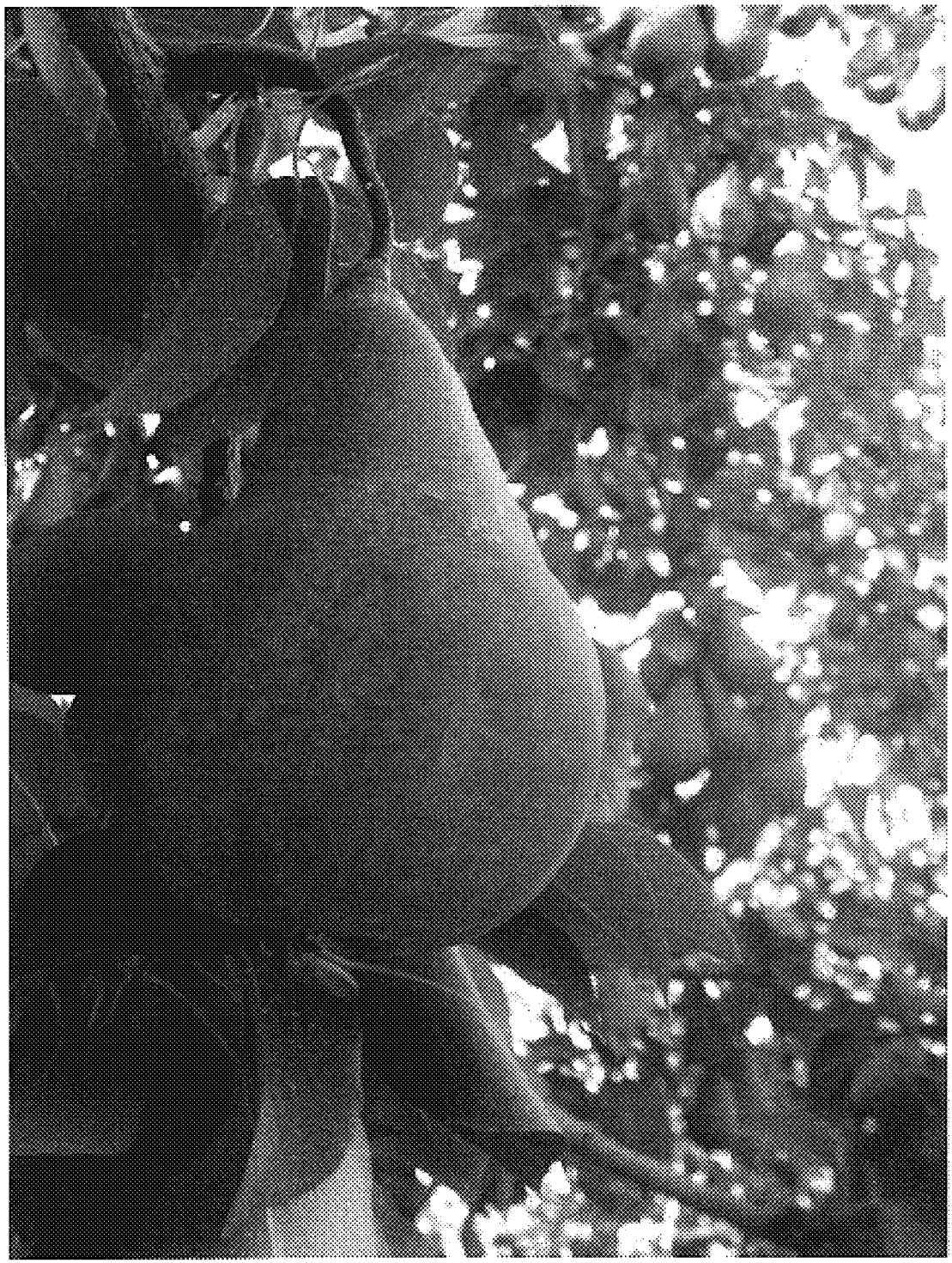
FIG. 3 shows fruit of the 'Todd' pear tree.
Figure 4:
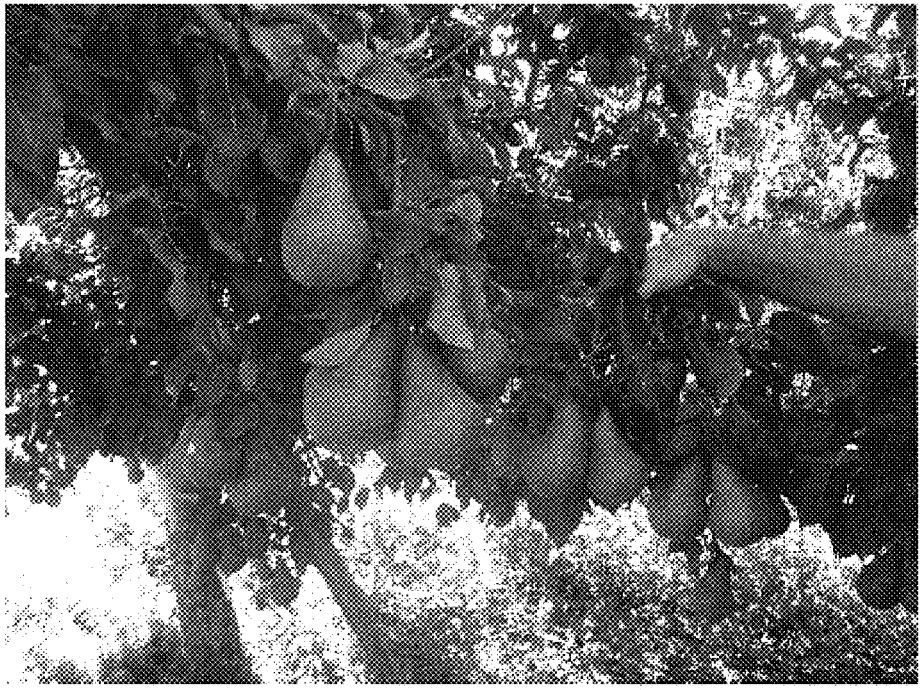
FIG. 4 shows fruit of the 'Todd' pear tree.
Figure 5:
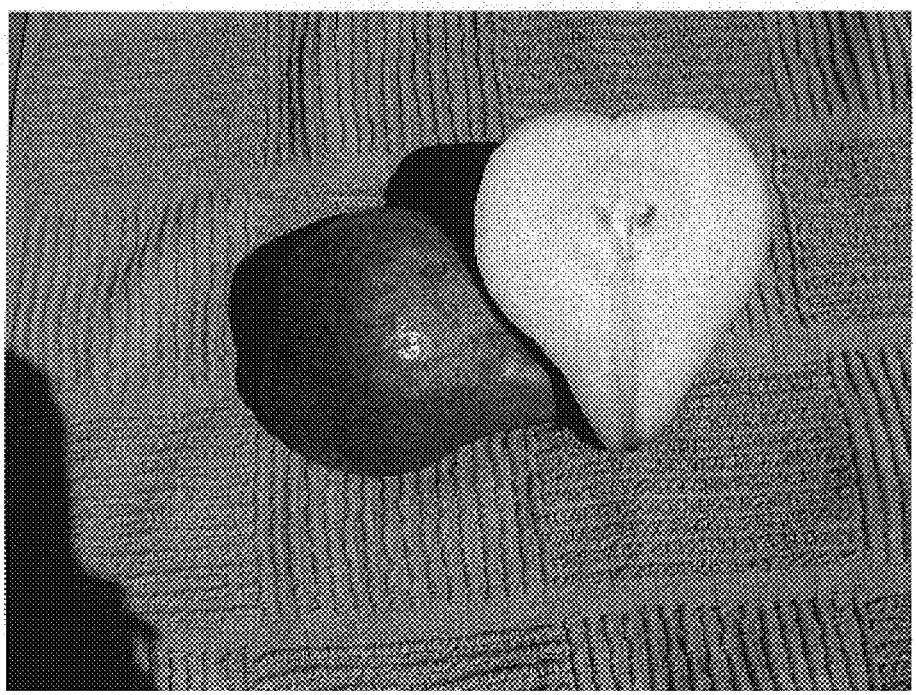
FIG. 5 shows a sectioned fruit of the 'Todd' pear tree.

The new cultivar 'Todd' originated as a limb sport mutation of 'Bosc' pear (not patented). It was discovered by the inventor in 1997 in a cultivated orchard at Entiat, Wash. and was first asexually propagated at Entiat in 2000. 'Todd' was further asexually propagated by budding at Parker, Wash., and has been shown to remain true to type over successive generations.

'Todd' is distinguishable from its parent and from other known Bosc-type varieties primarily by its large fruit.

DETAILED BOTANICAL DESCRIPTION OF THE VARIETY

The following detailed botanical description is based on observations made during the 2005 and 2007 growing seasons at Parker, Wash. The described trees were grown on Bartlett seedling rootstock, and were planted in 2003. All colors are described according to The Royal Horticultural Society Colour Chart. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree: Vigor — Moderate; Habit — Semi-erect; Size — Height 220 cm, spread 162 cm; Trunk — Diameter at soil level 8.7 cm, diameter at graft union 11.5 cm; Bark texture — rough near bottom, smoother above; Bark color — under color greyed-orange 175B, over color greyed-purple N187D.

Branch: Size — Length 91.2 cm, diameter 1 cm at base, 0.5 cm at tip; Crotch angle — 60°; Color — greyed-orange 176C.

Dormant one-year-old shoot: Pubescence — smooth; Size — diameter 0.4 cm, length 21 cm; Color — greyed-green 197A; Internode length — 2.5–3 cm; Lenticels — quantity 10 per square inch, color orange-white 159A, diameter 0.1 cm.

Flower: Bud — 6 per spur, round, length 1 cm, diameter 0.8 cm; color body white N155D, tip white N155D; Flower — diameter 3 cm, depth 1 cm; Petals — margin smooth, not touching, apex rounded, base equilateral, length 1.5 cm, width 1 cm, upper surface color white N155D, lower surface color white N155D; Pedicel — length 2 cm, diameter 1 cm, color yellow-green 149A; Sepals — 5 per flower, length 6 mm, color yellow-green N144D; Stigma — length 0.1 cm, color greyed-orange 166A; Style — length 0.8 cm, color white 155B; Ovary — length 0.5 cm, width 0.4 cm, color yellow-green 149A; Pistil — color white 155A, tip color greyed-orange 166A; Anthers — 20 per flower, 0.1 cm; Filament — length 0.5 cm; Pollen — color yellow 3B, semi-abundant; Bloom period — first bloom April 7, full bloom April 12; Pollenizers — 'Bartlett' or other pear variety that pollenizes 'Bosc' type varieties.

Leaf: Attitude in relation to shoot — upward; Size — length 8.0 cm, width 5.5 cm, length to width ratio 3:2; Shape — ovate, apex acuminate, base equilateral, margin smooth; Color — upper and lower surface yellow-green 146C; Petiole — length 4.5 cm; diameter 0.2 cm; color yellow-green 154D.

Fruit: Size — very large, diameter 10.5 cm at widest point, length 12.0 cm; Shape — Oblong pyriform; Position of maximum diameter — lower half; Color — Ground color yellow-green 152C, overcolor greyed-orange 163A, fully russeted; Eye — depth 0.5 cm, width 0.5 cm; Stalk — length 2.0 cm, diameter 0.5 cm at base, 1.0 cm at end, color greyed-orange 165A; Lenticels — present, diameter 0.1 cm; Flesh — firm, crisp, coarse, not gritty, medium juicy, sweet, color white 155B; Seeds — about 5 per fruit, oval, width 0.4 cm, length 1.0 cm, color greyed-purple 187A; Attractive fruit, good eating quality.

Yield: Heavy.
Use: Fresh market.
Resistance/tolerance to known pests/diseases: None noted.
Storageability: About 3 months in common storage.

What is claimed is:

1. We claim a new and distinct pear tree substantially as shown and described herein.

* * * * *